May 6, 1969 J. DE GRAAFF Plant Pat. 2,882
LILY PLANT
Filed Sept. 25, 1967
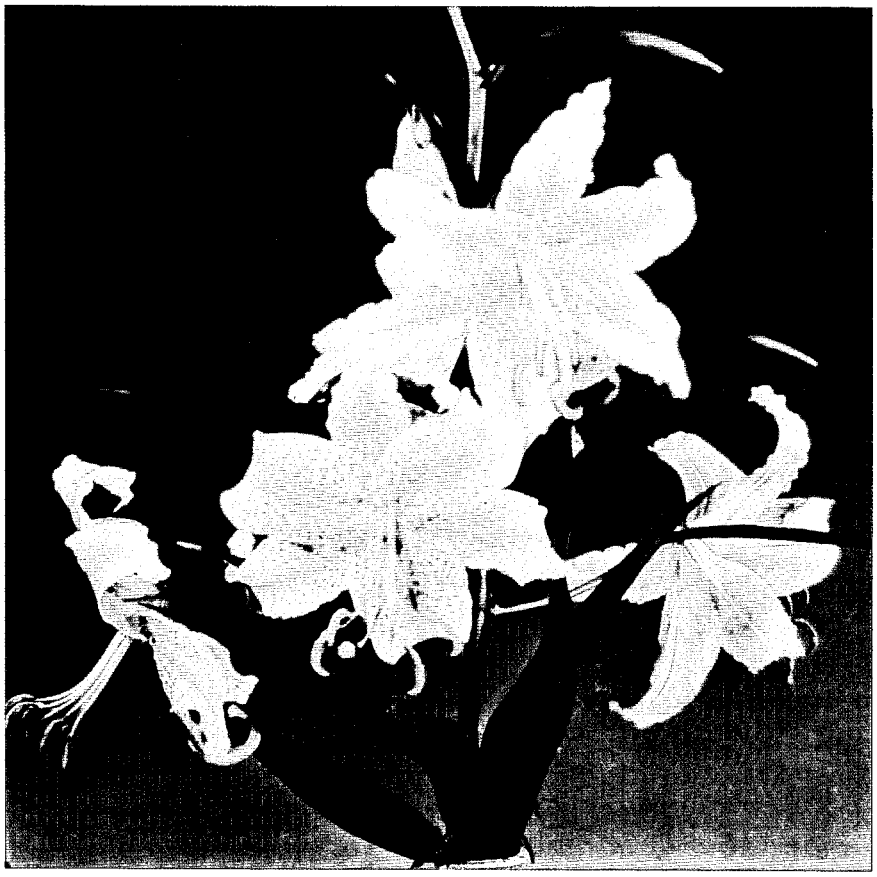
INVENTOR.
JAN DE GRAAFF
BY Rummler & Snow
Attys.

United States Patent Office

Plant Pat. 2,882
Patented May 6, 1969

2,882
LILY PLANT

Jan de Graaff, Gresham, Oreg., assignor to Oregon Bulb Farms, Division of Melridge Inc., Gresham, Oreg., a corporation of Washington Filed Sept. 25, 1967, Ser. No. 670,480
Int. Cl. A01h 5/02
U.S. Cl. Plt.—68 1 Claim

ABSTRACT OF THE DISCLOSURE

A new variety of Oriental hybrid lily plant bearing clusters of very large flowers of excellent form, strong color, and long persistence, both on the plant and as a cut flower; the new plant being particularly characterized by its vigor, its high bud count, its adaptability for pre-cooling and cold storage for prolonged periods, and its easy forcing capability whereby in greenhouse use the plant can be flowered the year around.

BACKGROUND OF THE INVENTION

My new variety of lily plant originated as a seedling *L. auratum cultivar* (unpatented), with *L. speciosum cultiver* (unpatented) as the pollen parent, and was developed by me in 1965 at Gresham, Oreg. in the course of a beeding program carried on by me since 1955 with the object of producing improved clones of *L. auratum* × *L. speciosum rubrum* which would combine the flower size of *L. auratum* and the beautiful color of *L. speciosum rubrum* together with hybrid vigor, high bud count, greater hardiness and disease resistance.

This new plant has been observed to possess substantially all of the desired characteristics of excellence of form, color and habit and thorough testing has shown the plant to force easily so that in greenhouse use it can be flowered at any time of the year. The new variety flowers with blooms of very large size, producing 12 or more flowers on a single stalk or stem, which are not affected by wet or hot weather and which possess a strong resistance to fungus, as observed at Gresham, Oreg.

My new variety of lily plant has been asexually reproduced by me and under my direction at Gresham, Oreg. and successive generations, produced by scaling of mature bulbs, have demonstrated that the novel and distinctive characteristics of the new variety are fixed and hold true, in all respects, from generation to generation.

DESCRIPTION OF THE DRAWING

My new variety of lily plant is illustrated in the accompanying photographic drawing which shows the full opened blooms in full color and illustrates the flower form, petal arrangement, and manner of disposition of the blossoms on the stalk.

DESCRIPTION OF THE NEW VARIETY

The following is a detailed description of my new variety of Oriental hybrid lily, with color designations according to the Horticultural Colour Chart of the Royal Horticultural Society:

*The plant*

Origin: Seedling.
Parentage:
- *Seed parent.*—*L. auratum cultiver* (unpatented).
- *Pollen parent.*—*L. speciosum cultiver* (unpatented).

Classification:
- *Botanic.*—*Lilium cultiver.* Division VII–D of classification Lilium,

- *Commercial.*—Oriental hybrid lily,

Form: Stem—single inflorescense.
Height: 5 to 6 feet.
Growth: Vigorous and upright. A sturdy, side-facing, and strong grower.
Foliage:
- *Quantity.*—Abundant.
- *Size of leaf.*—6 inches long. Shape—lanceolate.
- *Texture.*—Smooth and glossy.
- *Color.*—Upper side—dark green. Under side—lighter green.

Bulbs:
- *Size.*—About 2 inches, and larger, in diameter.
- *Color.*—White.

*The bud*

Form: Elliptical—ovoid and pointed,
Size: 5 to 6 inches long. 1 to 2 inches in diameter, increasing as bud develops,
Opening: Bud opens slowly,
Color: White, carmine center—crimson and silver when petals begin to unfurl.
Pedicel: 6 inches long. Sturdy, slender and upright. Color—light green.

*The flower*

Blooming habit: Annually, in August. Blooming once and profusely.
Size: Very large. 7 to 8 inches in diameter. Depth—1 inch,
Borne: In clusters, 12 and more on a single stem,
Shape: Cup shaped. Becoming flat as bloom matures, with recurving petals.
Petalage:
- *Number of petals.*—6.
- *Color*—Topside—Currant Red 821/3 at center, China Rose 024/2 near margins, and chalk white at edges. Reverse side—Dawn Pink 523/3.
- *Form.*—Lanceolate with prominent mid-rib.
- *Texture.*—Soft. Appearance.—satiny.

Fragrance: Flower is fragrant,
Effect of weather: Flower is not affected by hot or wet weather,
Lasting quality: 1 month on the plant; about 2 to 3 weeks as a cut flower,
Persistance: The flower tends to hang on its pedicel and dry,
Disease resistance: This plant has been observed to be resistant to fungus in the area of Gresham, Oreg. where this disease is prevalent.

*Genital organs*

Stamens:
- *Anthers.*—Of usual arrangement in the genus Lilium. 6 in number, each 3 inches long,
- *Filaments.*—2 inches long. Light green color.

Pollen: Color—rich brown.
Pistils: One, 4 inches long.
Stigmas: Green in color.
Ovaries: Green in color and of superior characteristics.

My new variety of Oriental hybrid lily most nearly resembles the variety Jillian Wallace (unpatented) and is particularly distinguished by its excellent form, color and growing habit. The new plant forces readily and therefore can be flowered as desired, at any time of the year. My new lily plant is further distingiushed by its ability to undergo precooling and cold storage for extended periods.

I claim:

1. A new and distinct variety of Oriental hybrid lily plant substantially as herein shown and described, characterized by the very large size and excellent form of its blooms, its greater hardiness and disease resistance, its adaptability to precooling and cold storage, its capability of being readily forced for greenhouse flowering at any time of the year, and by the long lasting quality of its blooms on the plant and as cut flowers.

No references cited.

ROBERT E. BAGWILL, *Primary Examiner.*